(12) United States Patent
Ridha

(10) Patent No.: US 12,251,151 B2
(45) Date of Patent: Mar. 18, 2025

(54) DIATHERMY TONSILLECTOMY SUCTION DISSECTOR APPARATUS

(71) Applicant: Hayder Ridha, Dubbo (AU)

(72) Inventor: Hayder Ridha, Dubbo (AU)

( * ) Notice: Subject to any disclaimer, the term of this patent is extended or adjusted under 35 U.S.C. 154(b) by 1032 days.

(21) Appl. No.: 17/268,217

(22) PCT Filed: Apr. 17, 2019

(86) PCT No.: PCT/AU2019/050339
§ 371 (c)(1),
(2) Date: Feb. 12, 2021

(87) PCT Pub. No.: WO2020/033989
PCT Pub. Date: Feb. 20, 2020

(65) Prior Publication Data
US 2021/0315630 A1    Oct. 14, 2021

(30) Foreign Application Priority Data
Aug. 13, 2018 (AU) .................. 2018902939

(51) Int. Cl.
*A61B 18/08* (2006.01)
*A61B 17/26* (2006.01)
(Continued)

(52) U.S. Cl.
CPC ............ *A61B 18/082* (2013.01); *A61B 17/26* (2013.01); *A61B 2017/32113* (2013.01);
(Continued)

(58) Field of Classification Search
None
See application file for complete search history.

(56) References Cited

U.S. PATENT DOCUMENTS 3,247,592 A * 4/1966 Arden ............... A61B 17/3213
30/338
4,307,720 A   12/1981 Weber
(Continued)

FOREIGN PATENT DOCUMENTS

JP    2012514490 A    6/2012

OTHER PUBLICATIONS

Annotated Castanon (Year: 2024).*
International Search Report & Written Opinion dated Jul. 17, 2019 from PCT Application No. PCT/AU2019/050339.

*Primary Examiner* — Linda C Dvorak
*Assistant Examiner* — Nicholas S Borsch
(74) *Attorney, Agent, or Firm* — INNOVATION CAPITAL LAW GROUP, LLP

(57) ABSTRACT

Diathermy tonsillectomy suction dissector apparatus has a body having a proximal handle, a distal curved tip and a diathermy cutting blade member slidably retained within the body to selectively extend from the tip. The diathermy cutting blade member comprises a flexible metallic blade comprising a proximal electrical connector socket and a hand operable electrically insulative position locking mechanism attached to the blade. The locking mechanism is hand operable via apertures and interlocks therewith to position the diathermy cutting blade member between retracted and extended positions and to lock the diathermy cutting blade member at the extended position.

15 Claims, 15 Drawing Sheets

(51) Int. Cl.
*A61B 17/3211* (2006.01)
*A61B 18/00* (2006.01)

(52) U.S. Cl.
CPC ............... *A61B 2018/00178* (2013.01); *A61B 2018/00327* (2013.01); *A61B 2018/00595* (2013.01); *A61B 2018/00601* (2013.01); *A61B 2018/00607* (2013.01); *A61B 2217/005* (2013.01)

(56) References Cited

U.S. PATENT DOCUMENTS

| | | | |
|---|---|---|---|
| 5,071,418 A | | 12/1991 | Rosenbaum |
| 5,318,565 A | | 6/1994 | Kuriloff et al. |
| 5,766,166 A | * | 6/1998 | Hooven ............. A61B 18/1445 606/45 |
| 5,878,938 A | * | 3/1999 | Bittner ............. A61B 17/07207 227/175.4 |
| 6,293,945 B1 | | 9/2001 | Parins et al. |
| 6,361,532 B1 | * | 3/2002 | Burek ................ A61B 18/1402 606/49 |
| 9,907,621 B2 | | 3/2018 | Jayaraj |
| 2003/0014053 A1 | * | 1/2003 | Nguyen ............. A61B 18/1445 606/51 |
| 2014/0182140 A1 | | 7/2014 | Rosenhan et al. |
| 2016/0157918 A1 | * | 6/2016 | Shvetsov ........... A61B 18/1477 606/42 |
| 2016/0249947 A1 | * | 9/2016 | Castanon ........... A61B 17/3213 606/167 |

\* cited by examiner

DIATHERMY TONSILLECTOMY SUCTION DISSECTOR APPARATUS

FIELD OF THE INVENTION

This invention relates generally to tonsillectomy apparatus. More particularly, this invention relates to tonsillectomy apparatus selectively configurable between dissection, cautery dissection and suction and suction only modes of use.

BACKGROUND OF THE INVENTION

Tonsillectomy is a surgical procedure in which both palatine tonsils are removed from a recess in the side of the pharynx called the tonsillar fossa.

One type of tonsillectomy procedure comprises the use of an elongate cutting blade for the dissection of the tonsils, typically held in one hand whilst another hand uses forceps to hold the tonsils.

A vacuum suction tip may be used to remove fluids (blood and saliva) during the procedure. The Yankauer tip (tonsil tip) is one of the most commonly used suction tips.

However, the utilisation of three instruments requires an assistant or alternatively the substitution of instrumentation as required, complicating and prolonging the procedure.

Furthermore, whilst the Yankauer tip allows for aspiration of large volumes of fluid, the Yankauer tip has the disadvantage of easily occluding when the tip is brought into close approximation with tissues or large blood clots. Surgeons often place a gauze sponge over the tip and suctioning fluid through the gauze to prevent occluding clogging.

The present invention seeks to provide a tonsillectomy suction dissector apparatus, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE DISCLOSURE

In accordance with a first embodiment, there is provided herein a tonsillectomy suction dissector apparatus comprising a proximal handle and a distal curved tip. The apparatus comprises a suction channel within and along the tip operably connecting at least one suction inlet port located at the end of the tip to a vacuum port of the handle for the suction of fluid in use. The apparatus further comprises a flexible cutting blade member slidably within slot along the tip and configurable by hand operable locking mechanism between an extended position wherein a distal cutting end of the cutting blade member extends from the end of the tip and a retracted position wherein the distal cutting end of the flexible cutting blade member is retracted within an end of the tip.

This retraction and extension of the blade allows dual functionality as suction tip or suction dissector, thus speeding the operation and reducing blood loss.

As such, the locking mechanism may be used for quickly reconfiguring the apparatus between dissection and suction and suction only modes of operation. Furthermore, the present configuration allows for one-handed dissection and suctioning, freeing the other hand for other tasks, such as manipulating forceps.

Furthermore, the present locking mechanism may allow for the reconfiguration of the apparatus with one hand, such as using the thumb only, freeing the forefingers for gripping the handle.

Specifically, the locking mechanism may comprise the flexible cutting blade member comprising a locking lever which interlocks locks within apertures through the handle. The cutting blade member may extend from a rear aperture of the handle for pushing forwards to the extended position wherein the locking lever locks within the superior apertures. Furthermore, the locking lever is accessible via the superior apertures to disconnect and pull the lever rearwardly to retract the cutting blade member.

The position of the suction holes towards the tonsillar fossa, where the bleeding happens, allowed instant suction of the blood at the exactly bleeding point, thus minimising the chance of blood accumulating in the throat, reducing risk of blood/clot inhalation.

Also, the position of the blade towards the surgeon, allows precise dissection and full visibility of the cutting place at all time, reducing the chance of inadvertently injuring surrounding tissues, and causing further bleeding Furthermore, the configuration of the suction inlet ports may substantially reduce or eliminate occlusion problems as may be experienced by the Yankauer tip. Specifically, the suction inlet ports may be located inferiorly with respect to the distal cutting end and may be arranged on differing faces of the end of the tip so as to prevent occlusion by pressing against one surface thereof. Specifically, in embodiments, the suction inlet ports may comprise a pair of distally located, oppositely laterally located and inferiorly located suction inlet ports.

In accordance with a second embodiment, there is provided a diathermy tonsillectomy dissector similarly comprising the body having a proximal handle and a distal curved tip.

The dissector may comprise a diathermy cutting blade member within the body which comprises a flexible metallic electrically conductive cutting and diathermy blade which is slidably retained within an interior curved slot of the curved tip. Furthermore, the diathermy cutting blade member may further comprise an electrical connector socket for electrically connecting the blade.

Furthermore, the diathermy cutting blade member comprises a hand operable electrically insulative position locking mechanism attached to the blade. The locking mechanism is hand operable via apertures within the body to configure the blade between retracted and extended positions wherein, in the extended position, the distal end of the blade extends beyond the tip for diathermy cutting.

The locking mechanism may be made of plastic so as to be electrically insulative and is attached to the cutting blade so as to avoid electrical contact when operating the locking mechanism via the apertures.

The locking mechanism may comprise a lever connected by a hinge (such as a live hinge) to a base. The base may be attached to the blade via inferior bosses which key within corresponding apertures of the blade.

The lever may comprise a rearward knob which locates within a rearward major aperture between the retracted and extended positions. The apertures may further comprise a forward minor aperture and the lever may further comprise a catch comprising a forward angle so as to slide under a bridge between the apertures so as to immovably engaged against the bridge so as to hold the blade in the extended position. To release the blade, the rearward knob of the lever is depressed downwardly within the aperture which disengages the catch allowing the locking mechanism to be pulled rearwardly by the rearward knob (and under action of a compression spring in embodiments).

The electric socket may be formed by a rear of the blade wherein sides thereof form an encirclement forming the socket.

In this way, an electrical connector comprising an electrical rod may be inserted into the socket. The socket may comprise a diameter slightly less than that of the rod and may comprise a lengthwise expansive break, thereby allowing the socket to expand slightly to accommodate and frictionally engage the rod.

Furthermore, the apparatus may comprise a rearward insulative button engaging the rear of the blade and concealing the socket from inadvertent electrical contact. In this way, when the electrode rod is inserted into the socket, the rearward insulative button may yet be used in the normal manner to extend and retract the blade whilst avoiding electrical contact with the blade. An angled boot may angle an electrical cable at a convenient angle from the socket.

In embodiments, the apparatus may comprise a wedge between a distal end of the blade and the tip so as to stabilise the distal end of the blade in operation, especially in that aluminium may be slightly flexible.

The wedge may be fastened to the distal end of the blade and may be substantially planar so as to stabilise the blade along at least a portion of the blade. The wedge may comprise inferior buses which key within corresponding apertures of the blade.

The wedge may be configured such that in the extended position, the wedge does not extend from beyond the tip.

According to one aspect, there is provided diathermy tonsillectomy suction dissector apparatus comprising: a body having a proximal handle, a distal curved tip and a diathermy cutting blade member slidably retained within the body to selectively extend from the tip, wherein the diathermy cutting blade member comprises a flexible metallic blade comprising a proximal electrical connector socket and a hand operable electrically insulative position locking mechanism attached to the blade, the locking mechanism hand operable via apertures and interlocking therewith to position the diathermy cutting blade member between retracted and extended positions and to lock the diathermy cutting blade member at the extended position.

The blade may be substantially planar and located within a rectangular cross-section slot.

The blade may comprise aluminium.

A proximal end of the blade may form the electrical connector socket.

Sides of the blade may form an encirclement forming the socket.

The apparatus may further comprise an electrical connector comprising an electrode rod for insertion within the socket.

The electrical connector socket may comprise a diameter slightly less than that of the electrode rod and comprising an expansive longitudinal break.

The apparatus may further comprise a rearward electrically insulative button concealing the socket therethrough.

The insulative button may define a rear face for pressing the cutting blade member towards the extended position.

The electrical connector may comprise an angled boot which poises an electrical cable thereof at an angle from the electrode rod.

The apparatus may further comprise a suction channel between at least one suction inlet port at the tip and a vacuum port at the handle.

The locking mechanism may comprise a pivotally coupled locking lever.

The locking mechanism may comprise bosses keying apertures of blade.

The locking mechanism may engage a compression member to bias the locking mechanism proximally.

The major aperture may comprise a length to accommodate a rearward knob of the lever between the retracted and extended positions.

The lever may comprise a catch which locates within the major aperture in the retracted extended position and in the minor aperture in the extended position.

The catch may comprise a proximal edge which locks rearwardly against a proximal edge of the minor aperture in the extended position.

The catch may comprise an angled distal face, which slides under a distal edge of the major aperture when the cutting blade member moves towards the extended position.

The apparatus may further comprise a restraining wedge at a distal end of the blade.

The wedge may be planar and may be connected to the blade.

According to another aspect, there is provided a diathermy tonsillectomy procedure using the apparatus as described herein, the method comprising connecting an electrical supply lead to the socket of the blade and hand operation of the locking mechanism via the apertures to position the diathermy cutting blade member to an extended position such that blade extends from the tip.

Hand operation of the locking mechanism via the apertures to position the diathermy cutting blade member to the extended position may comprise pressing a rearward insulative button of the diathermy cutting blade member.

Hand operation of the locking mechanism may further comprise hand operation of the locking mechanism via the apertures to position the diathermy cutting blade member to a retracted position comprising depressing a knob of a lever of the locking mechanism within a major aperture of the apertures such that a catch of the lever releases from a proximal edge of a minor aperture of the apertures Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which.

DESCRIPTION OF EMBODIMENTS

Figure 1:
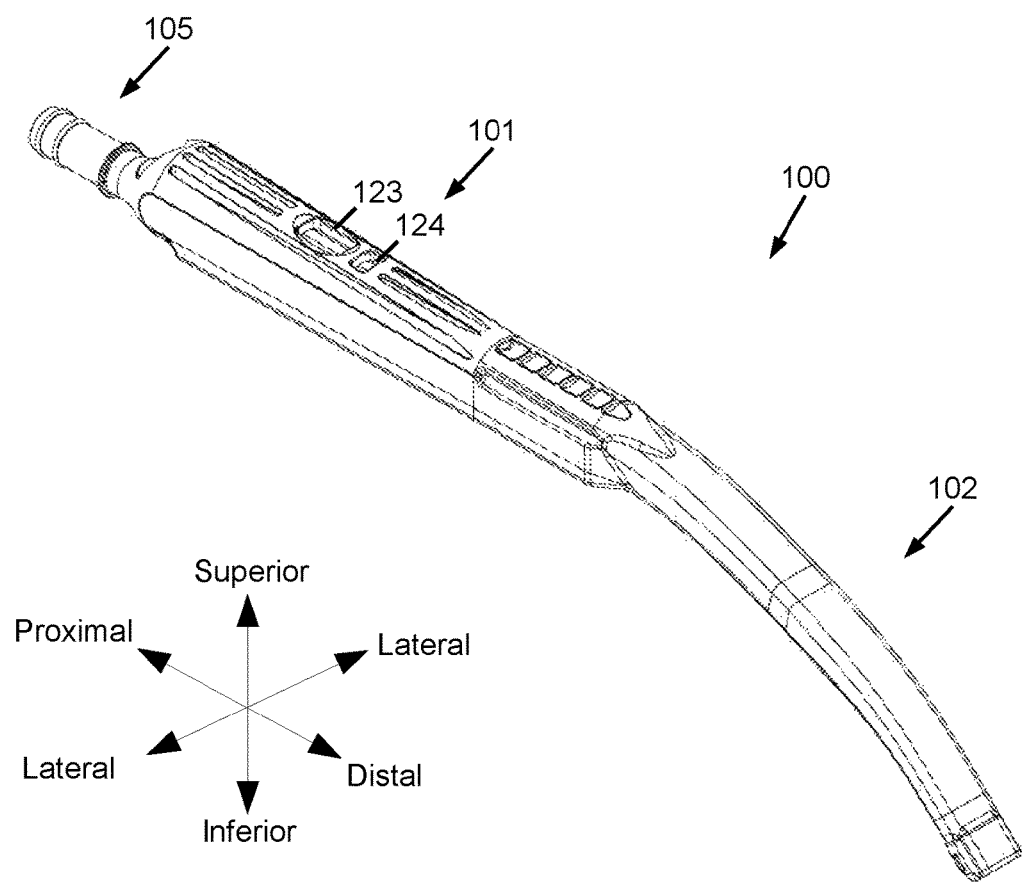
FIG. 1 shows a top perspective view of a tonsillectomy suction dissector apparatus in accordance with embodiments.

A tonsillectomy suction dissector apparatus 100 comprises a proximal handle 101 and a distal curved tip 102. The apparatus 100 may comprise at least one suction channel 103 operably connecting at least one suction inlet port 104 located at an end of the tip 102 and a vacuum tube connection 105 located at the handle 101.

Reference will be made herein to the orientational axes provided in FIG. 1 wherein the apparatus 100 is elongate comprising a near/proximal and a far/distal end, side/lateral sides and top/superior and bottom/inferior sides.

Figure 7:
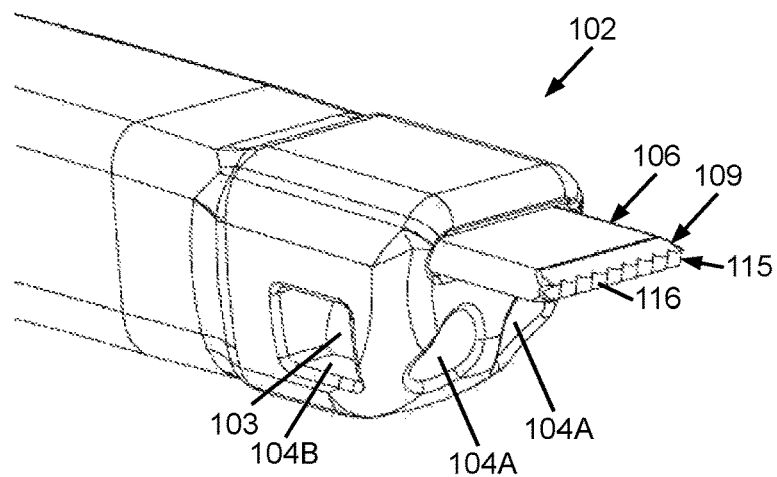
FIG. 7 shows a top perspective view of an end of the suction tip of the apparatus.
Figure 8:
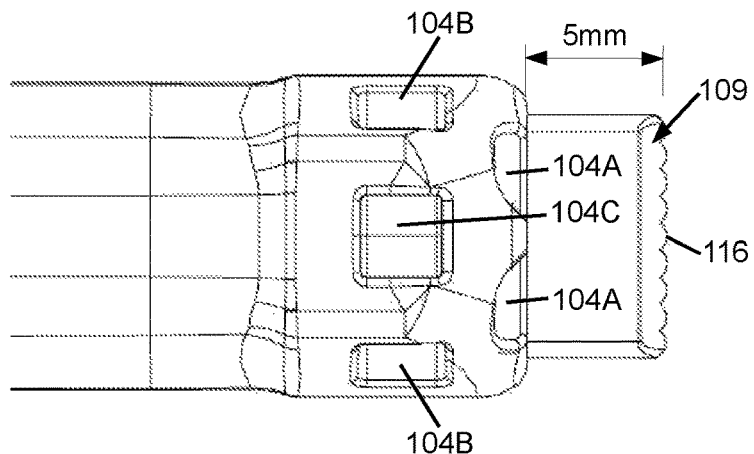
FIG. 8 illustrates a bottom plan view of the end of the suction tip.
Figure 9:
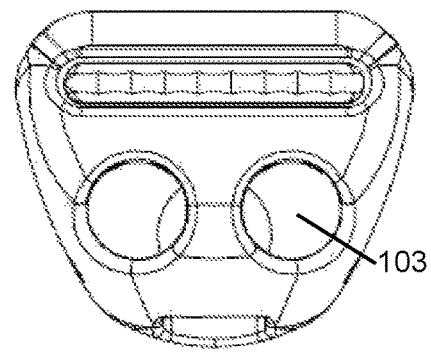
FIG. 9 illustrates a front elevation view of the end of the suction cup.
Figure 10:
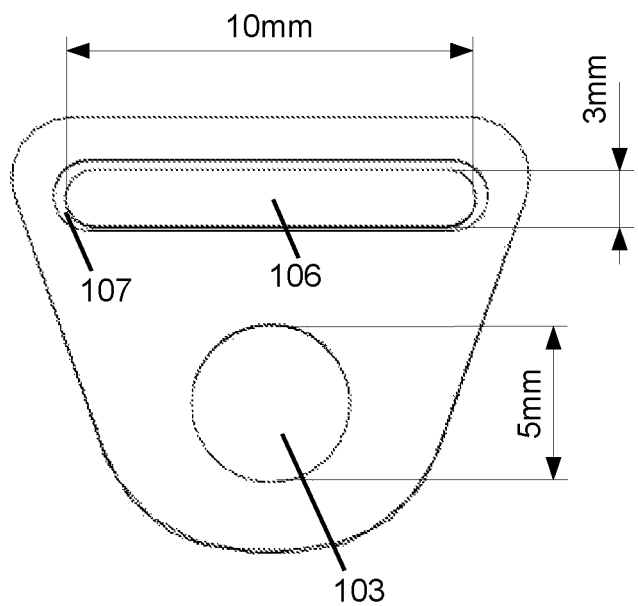
FIG. 10 illustrates a cross-sectional view of the tip of the apparatus.
Figure 11:
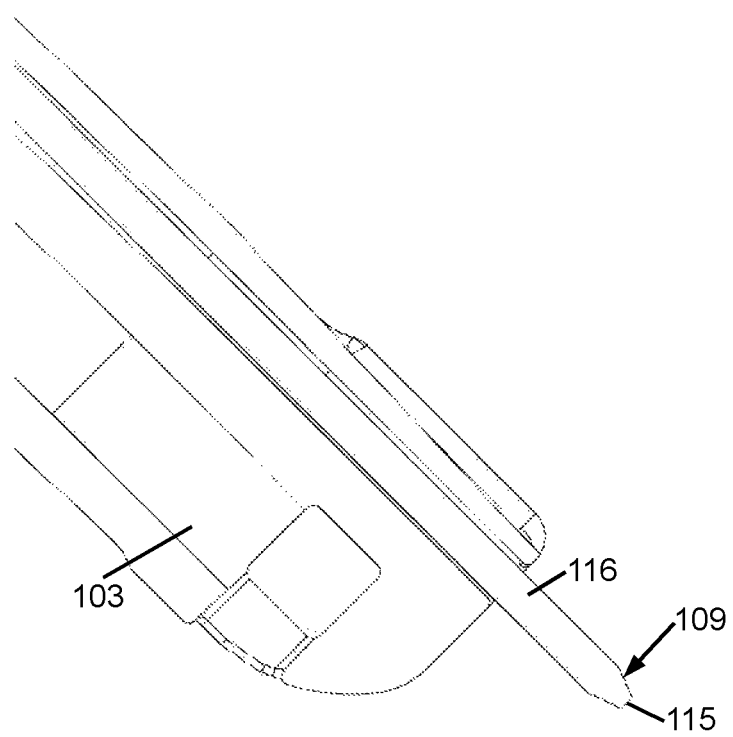
FIG. 11 illustrates a cross-sectional side view of the end of the tip of the apparatus.

The apparatus 100 further comprises a flexible cutting blade member 106 slidably retained within a slot 107 along the tip 102 and configurable by hand operable locking mechanism 108 at the handle 101 between an extended position wherein a distal cutting end 109 of the cutting blade member 106 protrudes from the end of the tip 102 as is substantially represented in FIGS. 7, 8 and 11, and a retracted position wherein the distal cutting end 109 is retracted within the end of the tip 102.

Utilisation of the apparatus 100 may comprise the connection of suction apparatus to the vacuum tube connection 105. The curved tip 102 is then inserted from a left or right side into the mouth such that the end thereof locates at the back of the throat. The locking mechanism 108 may be configured to extend the distal cutting end 109 of the cutting blade member 106 from the end of the tip 102 such that the distal cutting end 109 is able to dissect the respective tonsil, typically whilst being pulled with a pair of forceps on the opposite hand. The distal cutting end 109 defines an orthogonal straight cutting edge 115 which may be pushed forwardly against the base of the tonsil while the tonsil is pulled in the opposite direction of the forceps, thereby dissecting the tonsil.

While dissecting, fluids may be drained through the suction inlet ports 104. At any time, the surgeon may employ the locking mechanism 108 to retract the distal cutting end 109 to employ the tip 102 for suction alone, extending the distal cutting end 109 when and as required.

The procedure may be repeated for the opposite tonsil by inserting the curved tip 102 from the opposite lateral side of the mouth.

In a preferred embodiment, the handle 101 and the tip 102 are integrally formed from plastic. Furthermore, so too in embodiments is the cutting blade member 106 made from plastic. However, in embodiments, the cutting blade member 106 may be flexibly formed from metal so as to be electrically conductive for electrocautery application as is described in further detail below. This will allow triple functionality as suction, dissection and electro cautery, and instantly sealing the bleeding points. Also, employing electric coagulation in the instrument will reduce the need of using force to dissect scarred tonsils as the electricity will dissolve scar tissue, coagulate while minimal dissection force is applied, leading to more precise dissection, less tissue trauma, thus quicker and less painful healing post operatively.

Figures 3, 4:
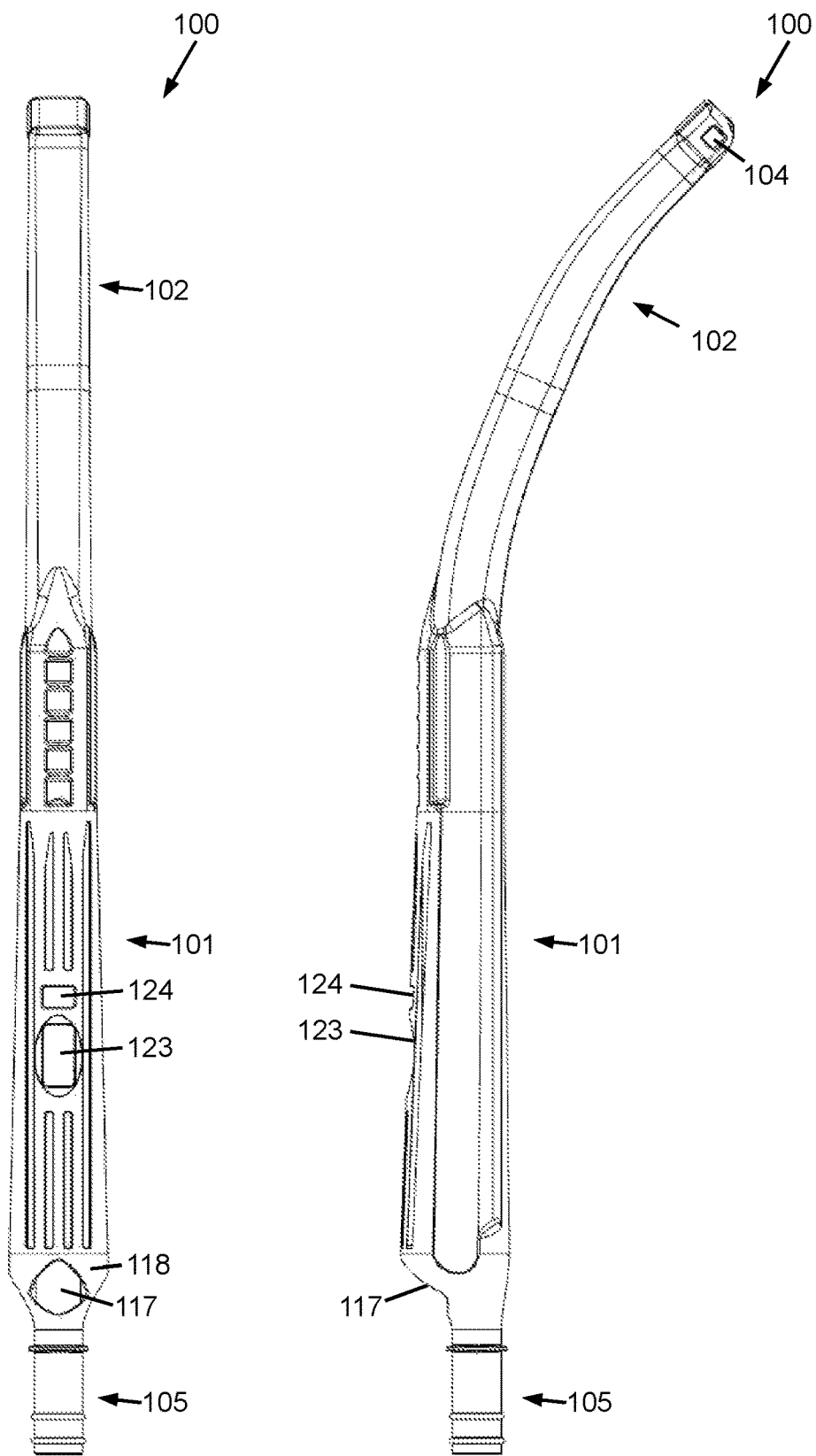
FIG. 3 illustrates a top plan view of the apparatus.
FIG. 4 illustrates a side elevation view of the apparatus.

With reference to FIG. 4, the handle 102 may be generally elongate, thereby having an elongate axis and the tip 102 may curve from substantially in-line with the elongate axis of the handle 101 to deviate by approximately 40° therefrom at a distal end thereof. This 40° curvature, takes away the surgeons hands outside the operating field ensuring constant visibility, at the same time 40° smooth curvature maintained adequate suction power inside the suction port and prevent the blood clogging inside the suction port.

Figure 2:
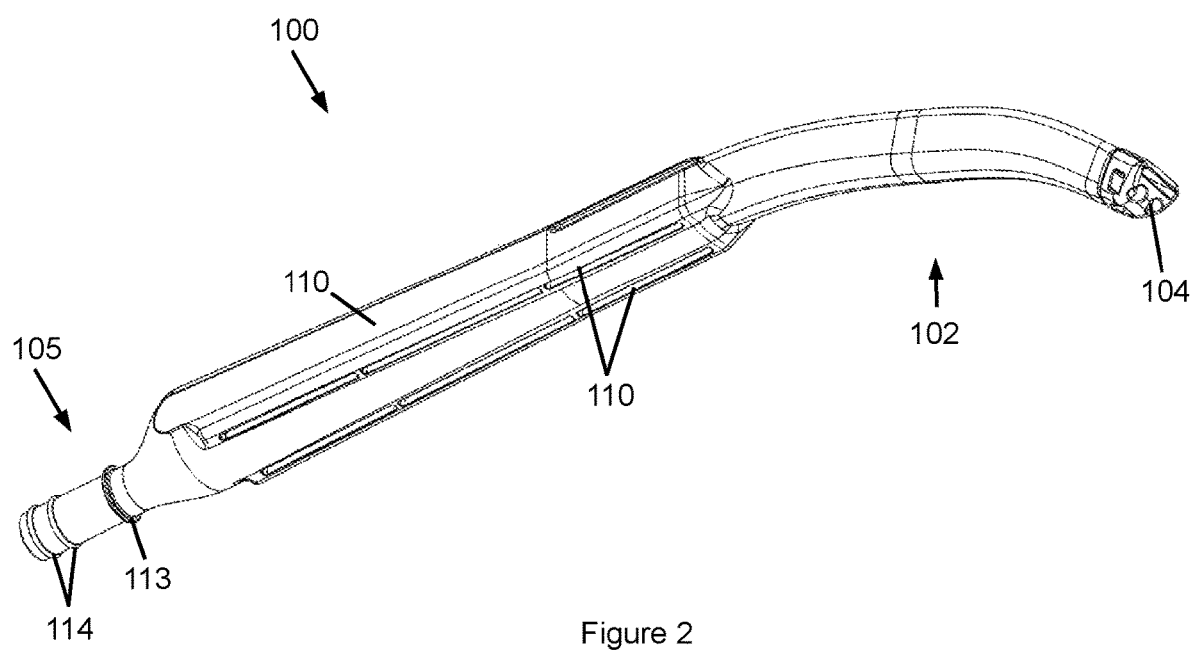
FIG. 2 illustrates a bottom perspective view of the apparatus.

With reference to FIGS. 1 and 2, the vacuum connection port 105 may extend from a proximal end of the handle 102. In the embodiment shown, the vacuum connection port 105 is generally cylindrical comprising an elongate axis substantially in line with an elongate axis of the handle 101. The vacuum connection port 105 may comprise connection interlock annuli 112 and O-ring seal 113.

FIG. 7 illustrates the end of the tip 102 in further detail showing the cutting blade member 106 in the extended position.

In a preferred embodiment shown, the cutting blade member 109 has a section which is flattened and orientated widthwise within the lengthwise slot 107 so as to be able to flex within the slot 107 when transitioning between the extended and retracted position. In one embodiment, the cutting blade member 109 may comprise a width of approximately 10 millimetres and a thickness of approximately 2 mm.

In a preferred embodiment, the cutting blade member 106 is manufactured from plastic.

As is illustrated in FIG. 7, the distal cutting end 109 may narrow to the orthogonal straight cutting edge 115.

Furthermore, the cutting edge 115 may comprise a plurality of serrations 116 running orthogonally across the cutting edge 115 from top to bottom which may engage the tonsil tissue to substantially prevent the cutting blade member 106 from slipping sideways during dissection and avoiding surrounding tissue damage.

As is best illustrated in FIG. 11, the cutting edge 115 is not sharpened to a point, thereby limiting the effectiveness of the cutting action thereof which may undesirably inadvertently damage surrounding tissue during manipulation, whilst yet comprising sufficient narrowness for being able to effectively cut the tonsils when required. For example, the width of the cutting edge 115 may be approximately 1 mm. Also, the blade dimensions are optimised to be big enough to dissect well, but small enough to maintain visibility, watching the surrounding tissues at all time to avoid collateral tissue damage.

With reference to FIG. 8, there is shown the distal cutting end 109 extending beyond the end of the tip 102 by approximately 5 mm in the extended position.

With reference to FIG. 7, there is illustrated the suction inlet ports 104 being located inferiorly with respect to the cutting blade member 106.

Furthermore, in a preferred embodiment, the suction inlet ports 104 may be located on multiple faces of the end of the tip 102 such as distally, laterally and inferiorly, thereby reducing likelihood of occlusion. Specifically, FIG. 7 shows the suction inlet ports comprising a pair of distal inlet ports 104A, a pair of opposite lateral suction inlet ports 104B and FIG. 8 shows an inferior inlet port 104C.

Figure 12:
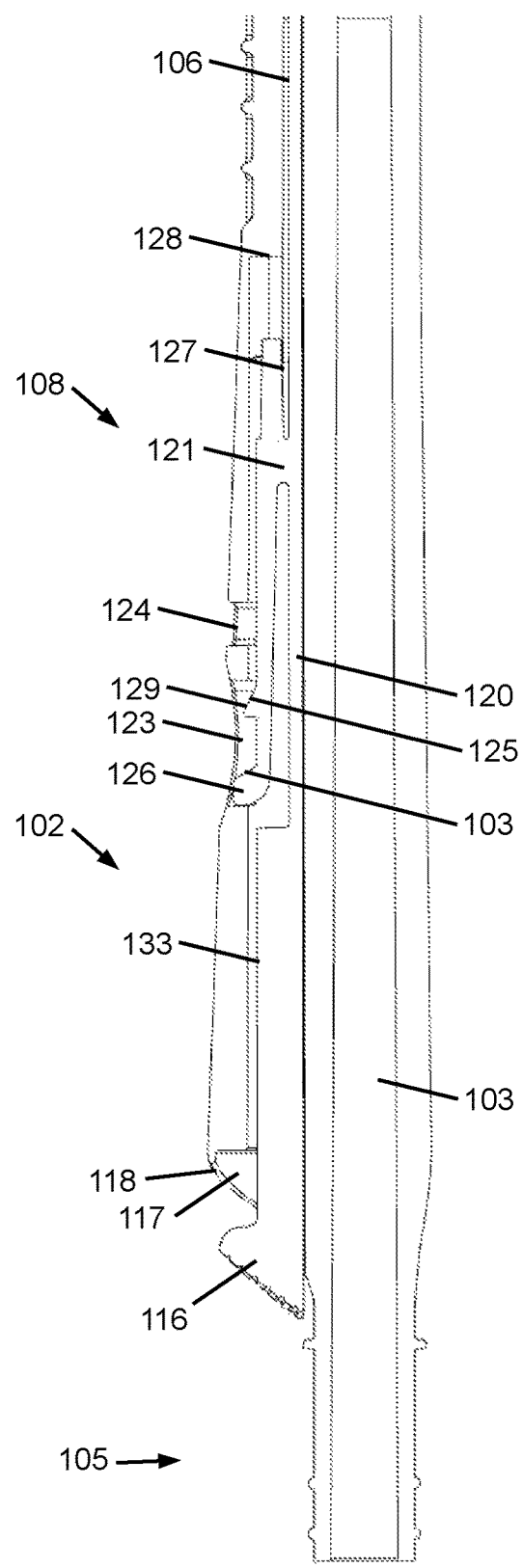
FIG. 12 illustrates a cross-sectional view of the handle of the apparatus.

FIG. 12 illustrates a cross-sectional view of the apparatus 100 showing the locking mechanism 100 in further detail. As is shown, the cutting blade member 106 may comprise a proximal end 116 extending from a rearward aperture 117 of the handle 102. A proximal face of the proximal end 116 is angled so as to occupy and mate flush with the proximal surface 118 of the handle 102 when located forwardly.

The cutting blade member 106 may further comprise a locking lever 119 pivotally coupled to an adjacent portion 120 by way of live hinge 121. Furthermore, a superior side 122 of the handle 102 may comprise a major rearward aperture 123 and a minor forward aperture 124 between which a catch 125 of the lever 119 is able to selectively transition. The lever 119 may comprise a rearward knob 126 accessible via the major aperture 123 to depress the lever 119. Furthermore, the lever 119 terminates distally with buttress 127 which abuts against opposing wall 128 when the cutting blade member 106 is in the extended position.

FIG. 12 shows the cutting blade member 106 in the retracted position. As such, in order to extend the cutting blade member 109 for dissection, the rearward end 116 may be pushed forwardly along the elongate axis of the handle 102, typically with the thumb whilst grasping the underneath of the handle 102 with the forefingers. The forward ramp 129 of the catch 125 depresses the lever 109 such that the catch 125 is able to transition under the intermediate portion 130 between the major and minor apertures 123, 124 until such time that the catch 125 locates within the forward minor aperture 124. Once in this location, the rearward orthogonal edge 130 of the catch 125 jambs against a forward edge 131 of the intermediate portion 130, preventing the cutting blade member 106 from sliding rearwardly under pressure. At this extended position, the buttress 127 may abut against the opposing wall 128 thereby limiting the forward travel of the rearward end 116.

Subsequently, in order to retract the cutting blade member 106, the thumb may be inserted within the major aperture 123 to substantially depress the lever 119 and to simultaneously pull rearwardly against the forward edge 132 of the knob 126 which disengages the rearward face 130 of the catch 125 from the forward edge 131 of the intermediate portion 130 and allowing the rearward sliding of the cutting blade member 106 under action of the thumb.

As can also be appreciated from FIG. 12, a rearward portion 133 of the slot 107 is sufficiently wide and so as to allow the entire rearward removal of the cutting blade member 106.

Figure 5:
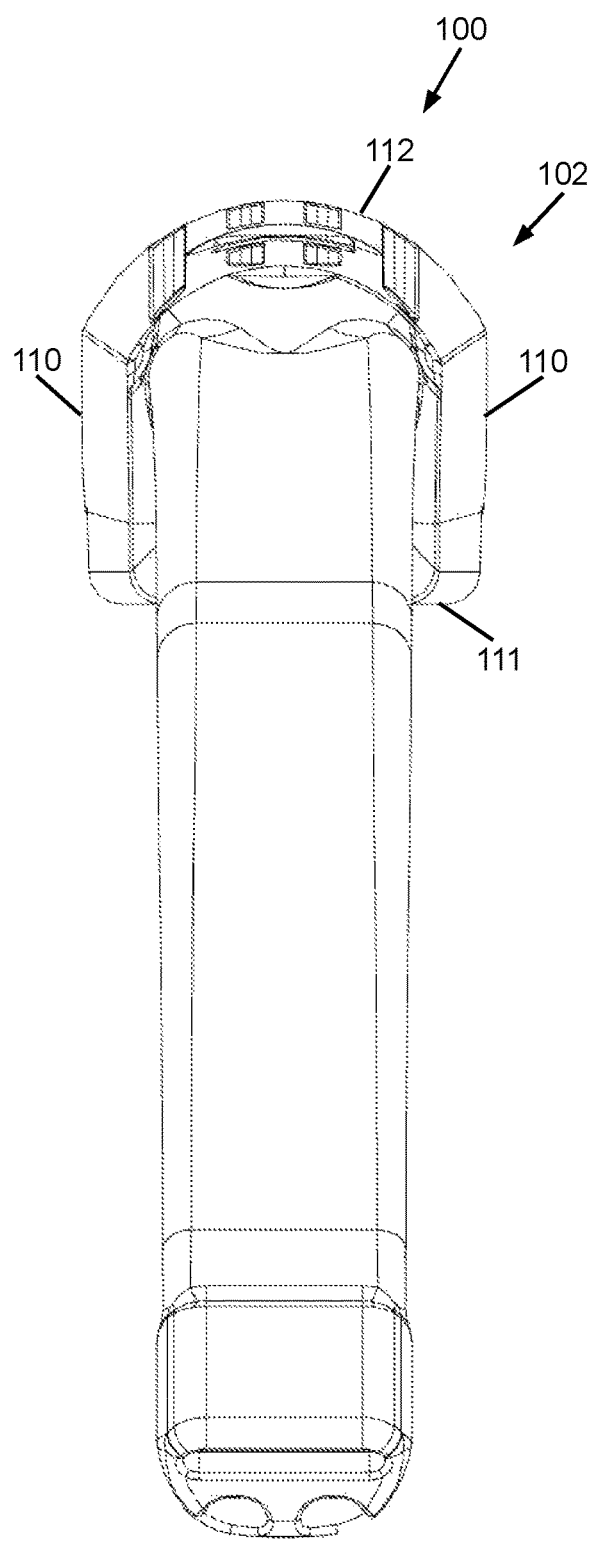
FIG. 5 shows a front elevation view of the apparatus.
Figure 6:
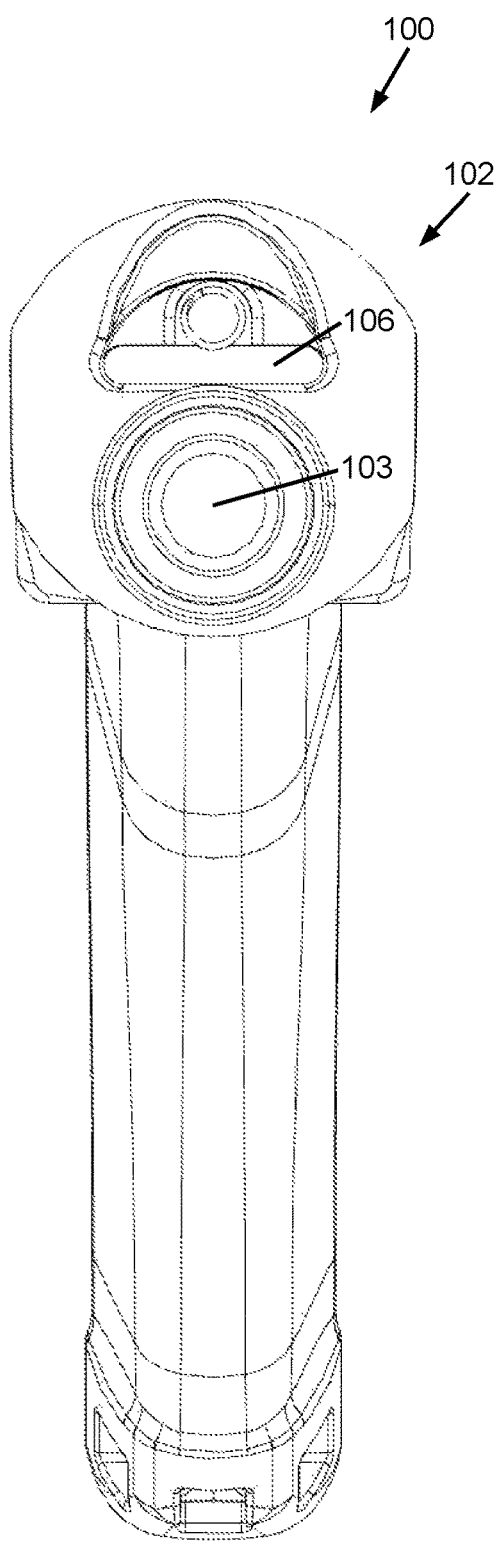
FIG. 6 shows a rear elevation view of the apparatus.

Whilst the locking mechanism 108 may be configured for thumb operation, the handle 102 may be shaped for enhancing the grip of the opposing forefingers. Specifically, with reference to FIG. 5, the panel 102 may comprise planar side walls and orthogonal inferior edges 111, conferring a non-circular cross-section to the handle 102, thereby preventing or reducing rotational slipping thereof within the surgeon's hand.

FIGS. 15-25 show a diathermy tonsillectomy suction dissector apparatus 140. In accordance with this embodiment, the apparatus 140 comprises a diathermy cutting blade member 141 comprising an electrically conductive metallic cutting blade 142.

Figure 20:
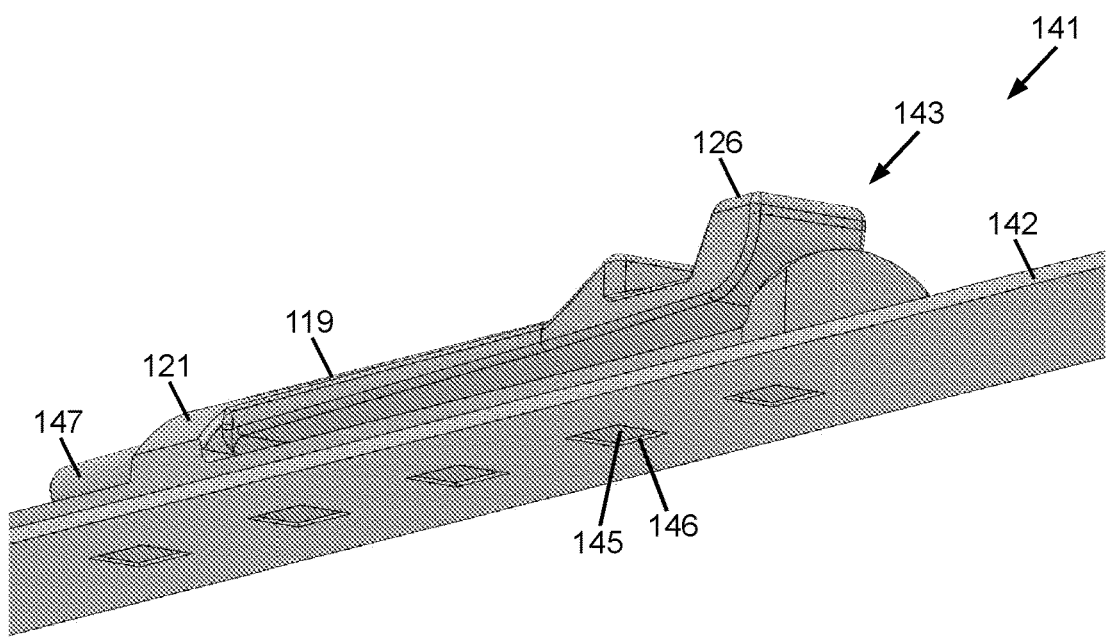
FIG. 20 shows an underside view of an insulative locking mechanism attachable to the electrically conductive blade of the diathermy suction dissector apparatus in accordance with an embodiment.
Figure 21:
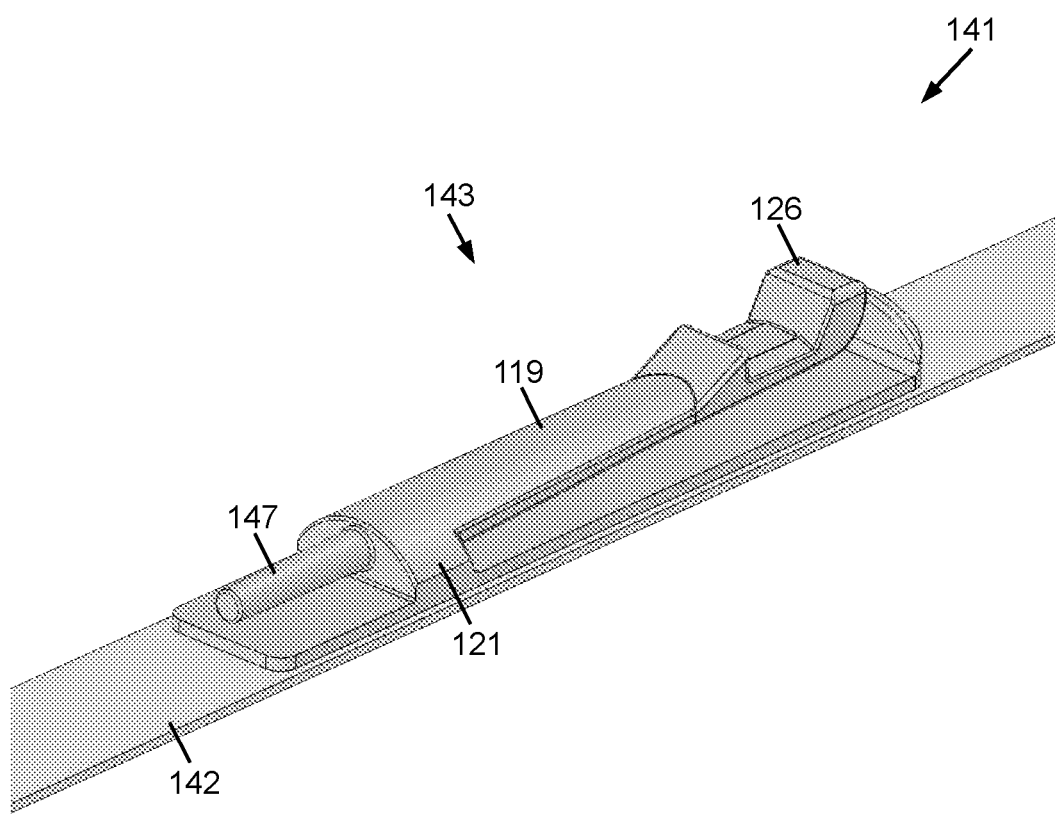
FIG. 21 shows a top perspective view of the insulative locking mechanism.

FIG. 20 illustrates an underside view of the diathermy cutting blade member 141 comprising the electrically conductive metallic cutting blade 142 comprising an electrically insulative position locking mechanism 143 coupled thereto.

In embodiments, the metallic cutting blade 142 may be made from aluminium and may be similarly flexible so as to be able to bend at the tip 102 of the apparatus 140 so as to be able to selectively extend in a similar manner described above for cutting, but also diathermy. The blade 142 may comprise a thickness of approximately 1 mm.

The insulative position locking mechanism 143 may similarly comprise the locking lever 119 pivotally coupled to a base 144 by way of live hinge 121. The base 144 may comprise a plurality of underside bosses 145 which key into corresponding apertures 146 cut from the metallic cutting blade 142.

The distal end of the mechanism 143 may comprise a barrel 147 for retaining a compression spring 148 thereabout 108 for pressing against an opposing wall 149 to bias the position locking mechanism 143 rearwardly towards a proximal end of the apparatus 140.

The lever 119 may also comprise the rearward knob 126 which selectively locates between the major aperture 123 and the minor aperture 124. Similarly, the lever 119 may comprise the catch 125 comprising the forward ramp 129 for sliding under the bridge 150 between the apertures 123, 124 so as to allow the cutting blade member 141 to slide forwardly against the compression of the compression spring 108 but to resist against the bridge 150 when pressure is applied to the distal end of the cutting blade 142.

Release and therefore retraction of the cutting blade 142 comprises depressing the knob 126 within the major aperture 123 to disengage the catches 125 from the bridge 150 and pressing against a forward face 151 thereof to retract the knob 126 rearwardly and therefore the entire diathermy cutting blade member 141.

The insulative position locking mechanism 143 may be made from plastic.

As can be appreciated, the composite structure of the diathermy cutting blade member 141 comprising the insulative position locking mechanism 143 and the metallic blade 142 connected thereunderneath prevents electrical contact with the electrically conductive metallic blade 142 via the apertures 123, 124 of the apparatus 140.

Figure 22:
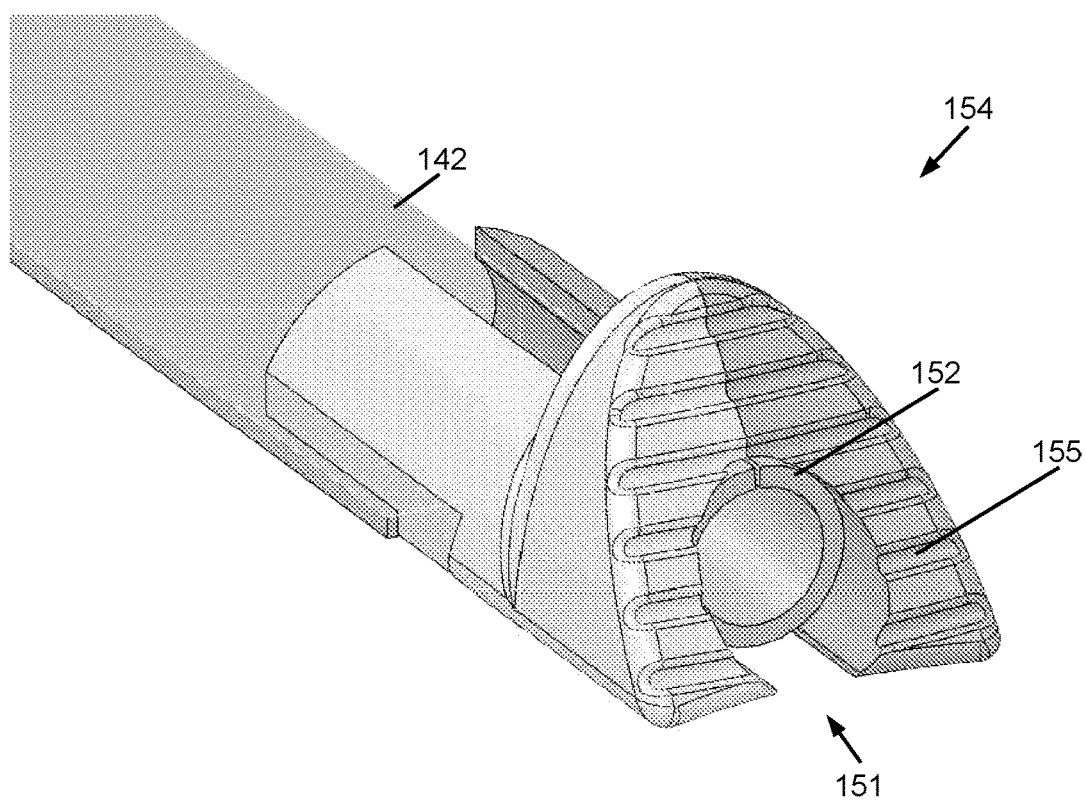
FIGS. 22 and 23 show a rear end of the electrically conductive metallic cutting blade and an insulative button around an electrical socket.
Figure 23:
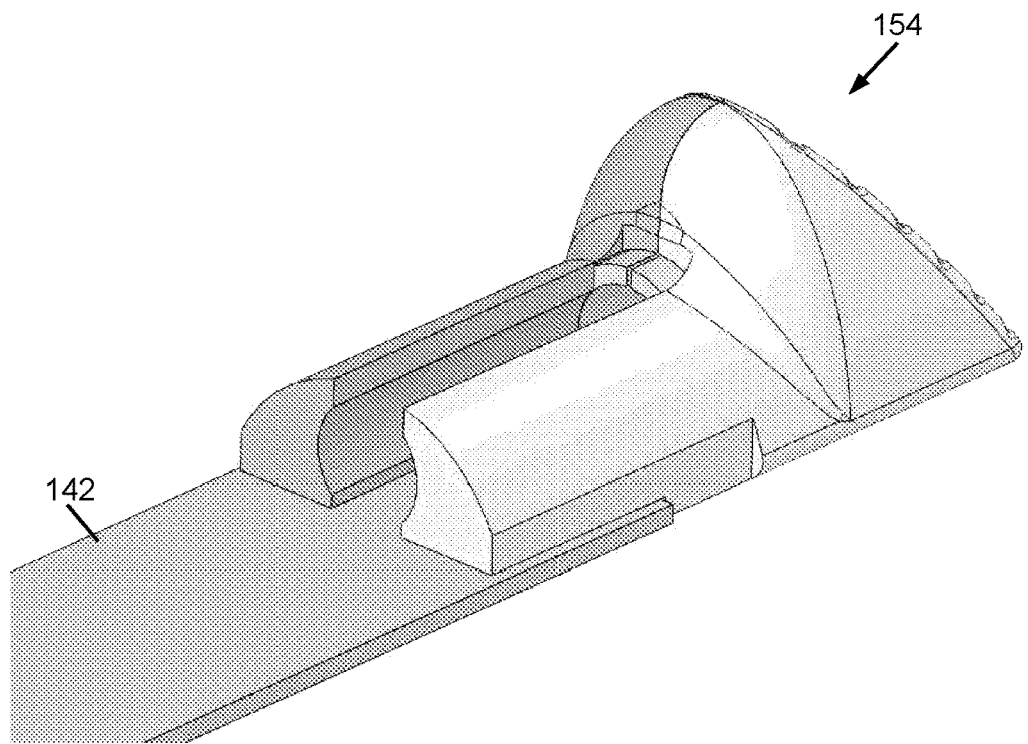

FIGS. 22 and 23 show a proximal end of the cutting blade 142 rolled into a barrel to form a socket 151 for a diathermy electrical lead 152. The diathermy electrical lead 152 may comprise an elongate electrode rod 153 which slides into the socket 151 and is frictionally engaged therein. In this regard, the socket 151 may comprise a diameter slightly less than that of the electrode rod 153 yet comprise a longitudinal break to allow the socket 151 to expand slightly, thereby accommodating and frictionally engaging the electrode rod 153 therein in use.

Figure 13:
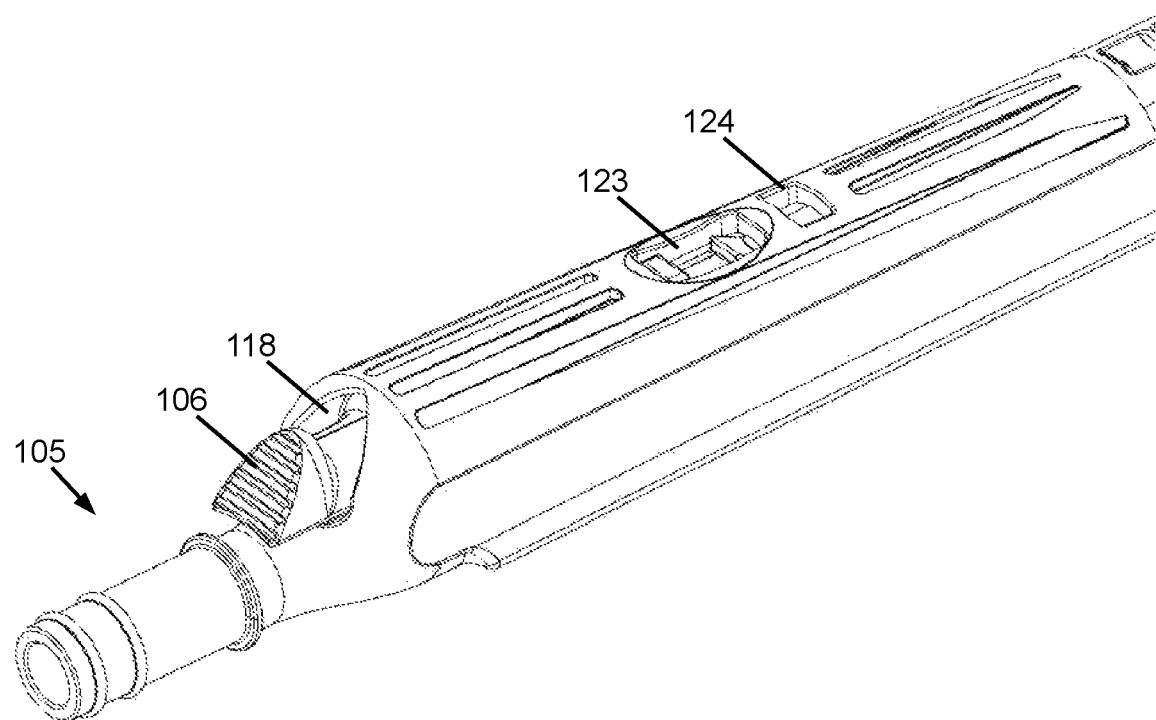
FIG. 13 illustrates the rearward position of the cutting blade member in the retracted position.
Figure 14:
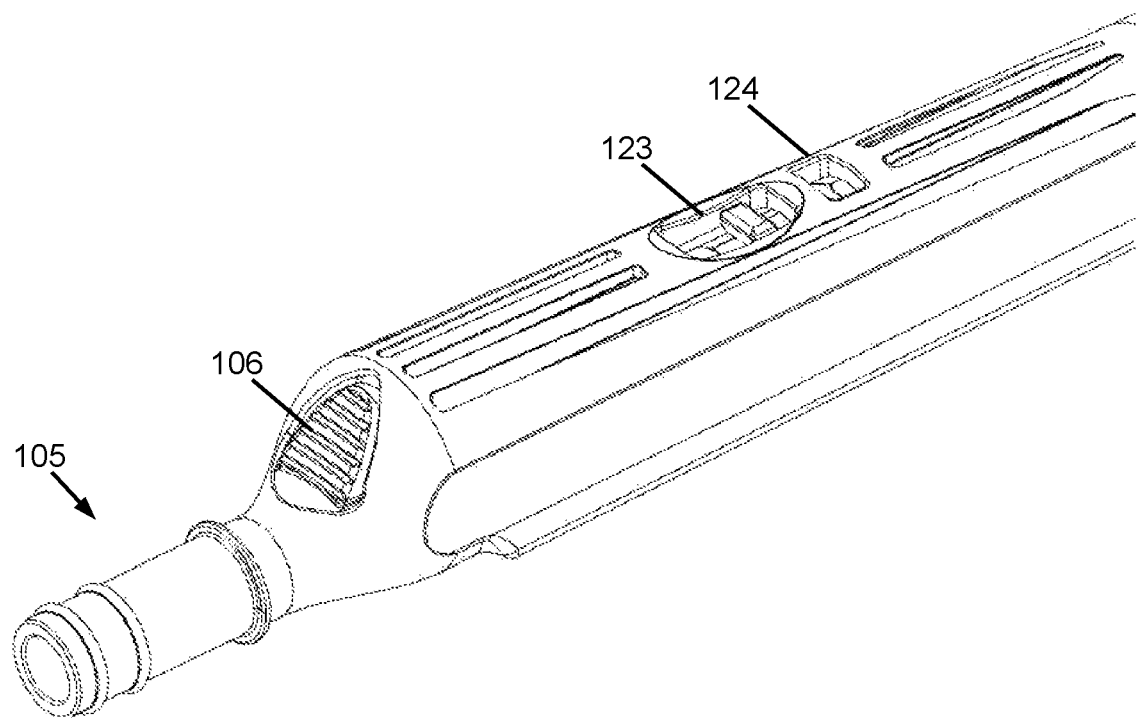
FIG. 14 illustrates the forward position of the cutting blade member in the extended position.
Figure 15:
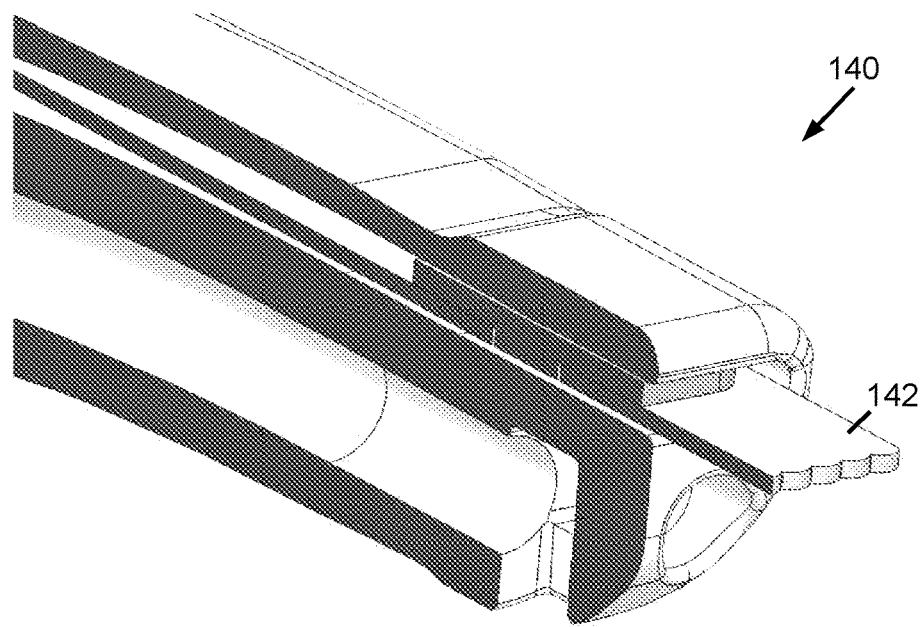
FIG. 15 shows a cross-sectional view of the tip of a diathermy suction dissector apparatus in accordance with an embodiment.
Figure 16:
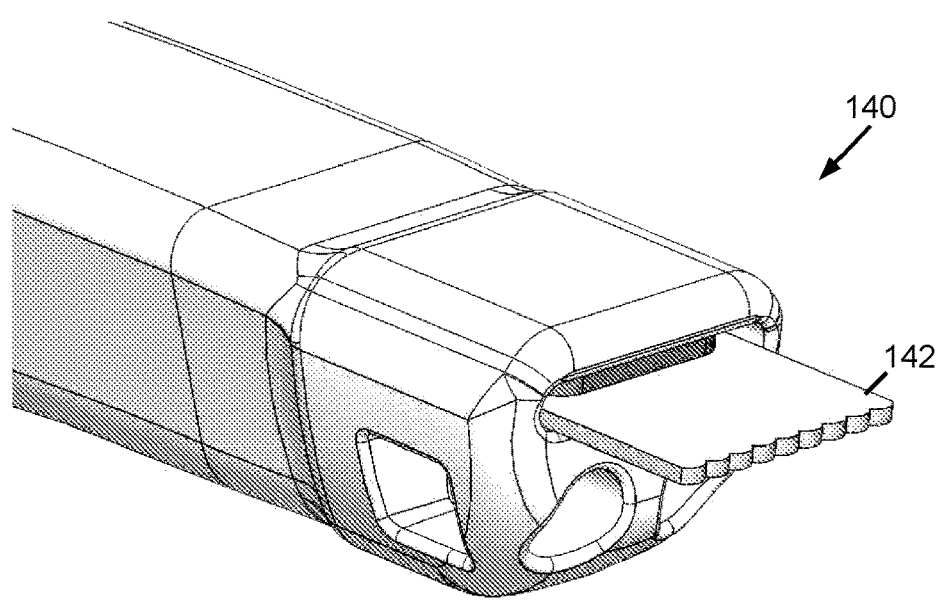
FIG. 16 shows a view of the tip of the diathermy suction dissector apparatus.
Figure 17:
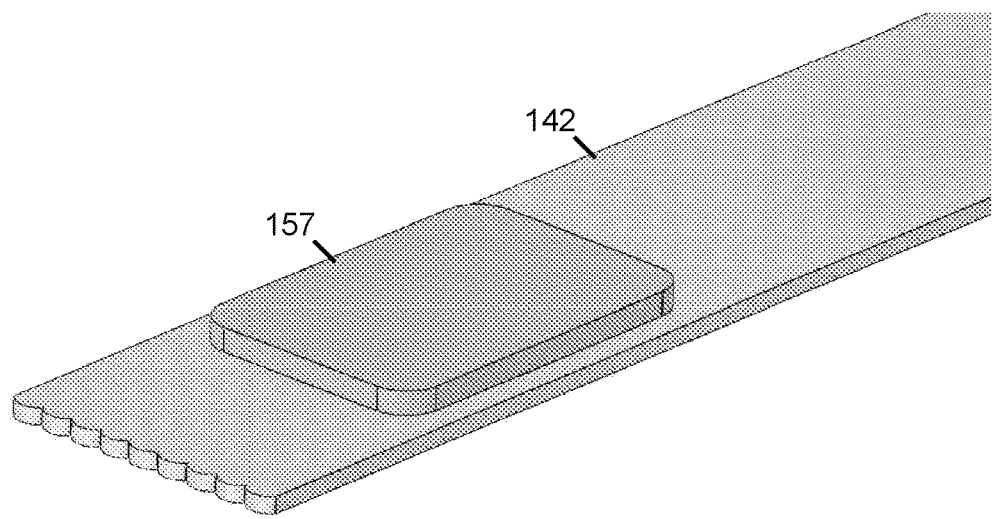
FIGS. 17 and 18 show respective top and bottom perspective views of a distal end of a metallic cutting blade of the diathermy suction dissector apparatus comprising a stabilising wedge.
Figure 18:
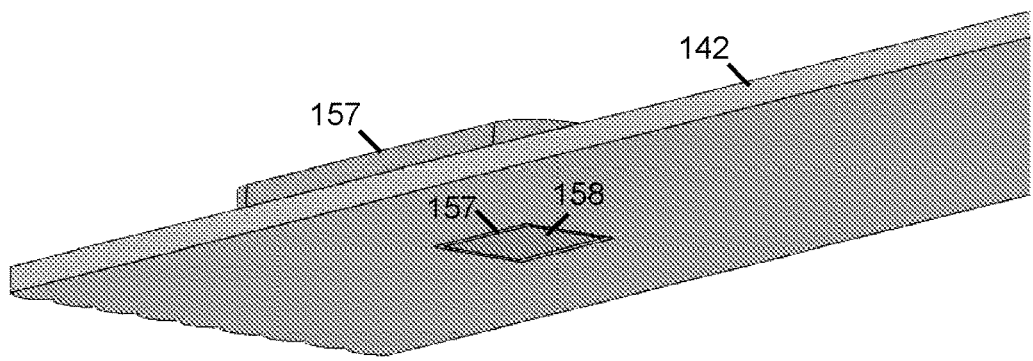
Figure 19:
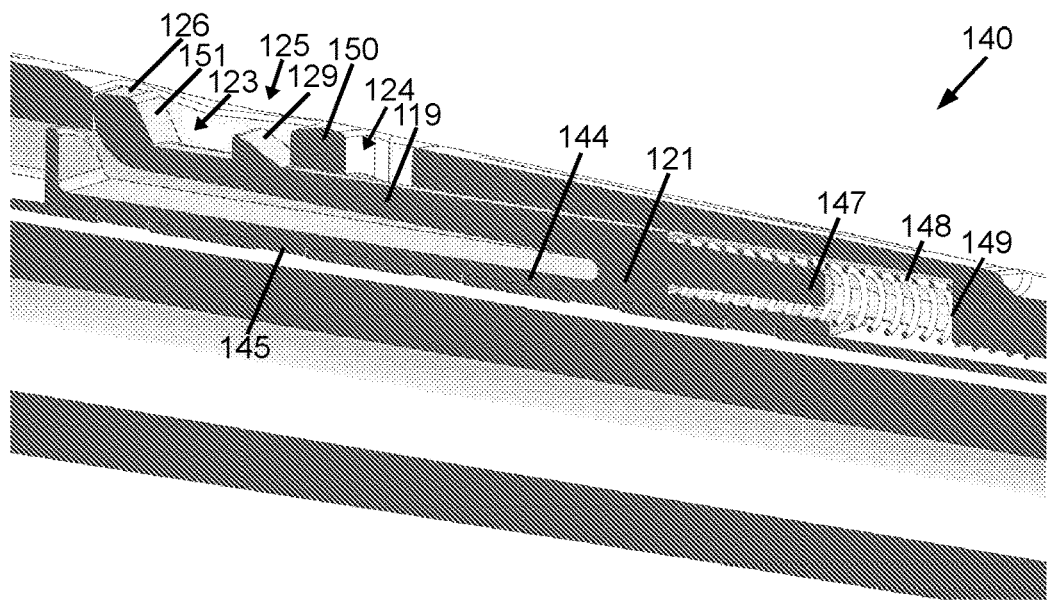
FIG. 19 shows a cross-sectional view of the locking mechanism of the diathermy suction dissector apparatus in accordance with an embodiment.

A plastic proximal button 154 may surround the socket 151. The button 154 may comprise the frictionally engaging angled face 155 allowing the diathermy cutting blade member 141 to assume the extended and retracted positions as is illustrated in FIGS. 13 and 14.

When the electrode rod 153 is engaged within the socket 151, the socket 151 and the electrode rod 153 are concealed from electrical contact. However, the rear face 155 of the proximal button 154 is yet able to be depressed with a finger to allow extension and retraction in in the normal manner.

Figure 24:
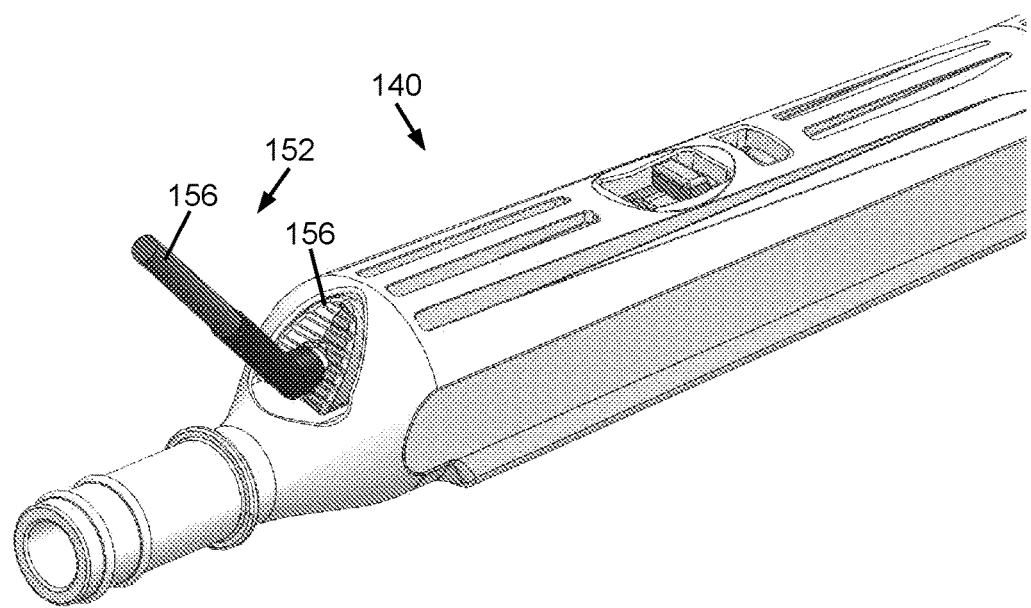
FIGS. 24 and 25 illustrate the connection of an electrical supply lead to the socket of the diathermy suction dissector apparatus in accordance with an embodiment.
Figure 25:
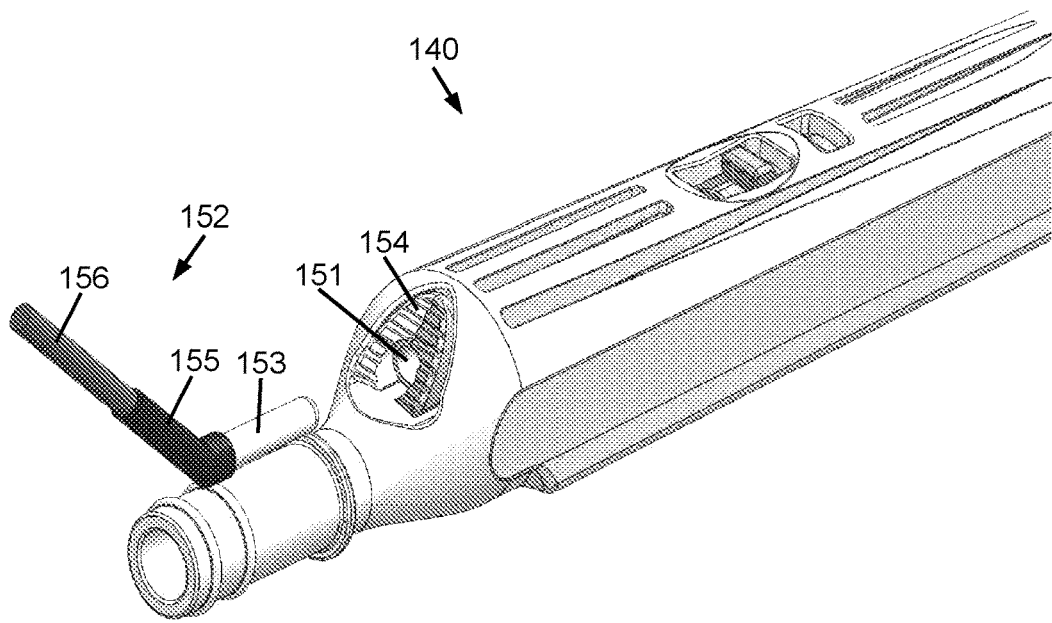

In the embodiment shown in FIGS. 24 and 25, the electrical lead 152 may comprise an angled boot 155 poising the electrical cable at a convenient angle from the socket 151.

FIGS. 15-18 illustrate the distal end of the cutting blade 142 comprising a distal wedge 157. The wedge 157 wedges between the metal cutting blade 142 and an interior surface of the lengthwise interior slot 107, thereby holding the distal end of the cutting blade 142 firm during operation.

In the embodiment shown, the wedge 152 is secured to a distal end of the cutting blade 142. In this regard, the wedge 157 may yet comprise an underside boss 158 which keys into a corresponding cut out 159 of the cutting blade one option 42.

In this way, the wedge 157 slides with the blade 142 within the slot 107. The wedge 157 may be made from plastic.

Figure 26:
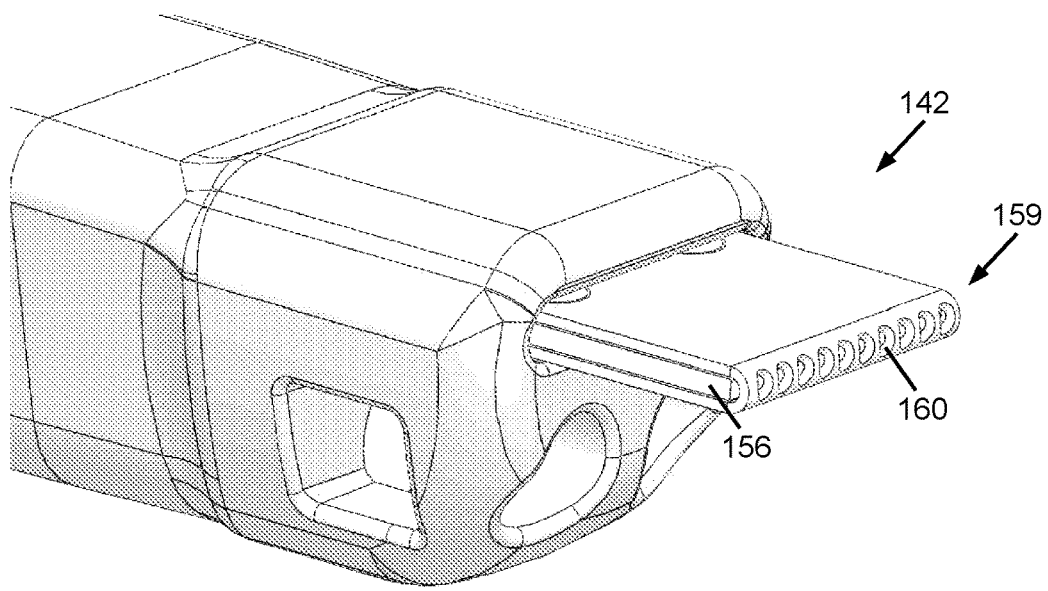
FIG. 26 illustrates a perspective view of distal end of the diathermy suction dissector apparatus with cutting blade extended in accordance with an embodiment.
Figure 27:
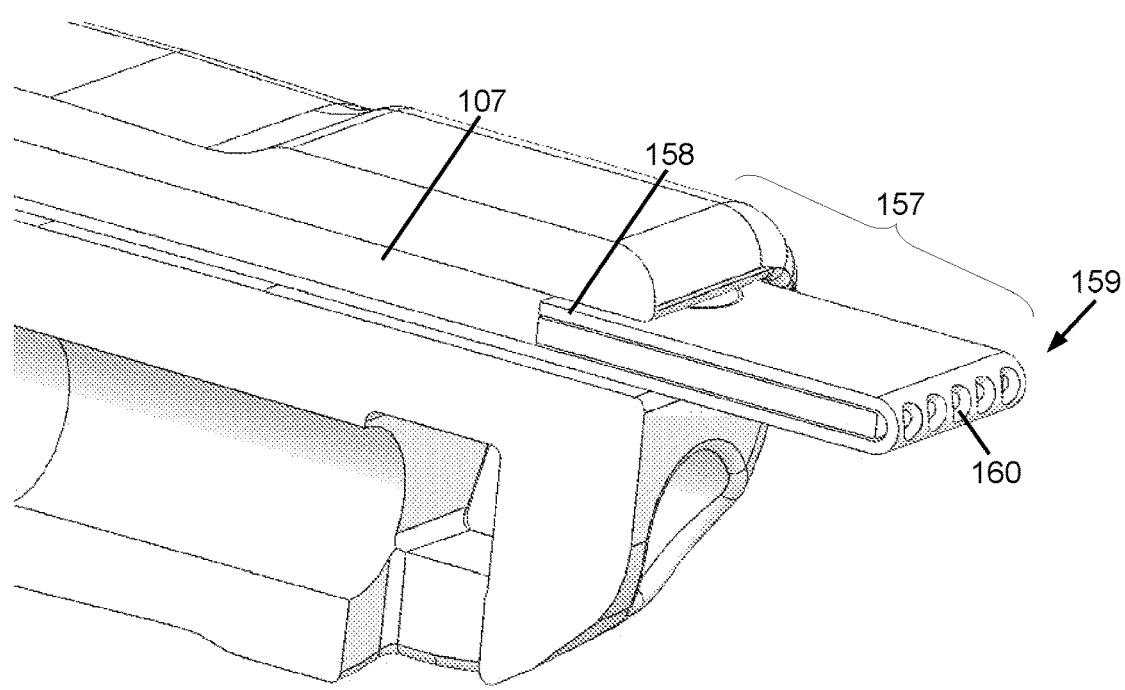
FIG. 27 illustrates a cross-sectional view of a distal end of the diathermy suction dissector apparatus with cutting blade extended in accordance with an embodiment.

FIG. 26 illustrates an embodiment wherein the metallic cutting blade 142 is folded back at a distal end thereof around a substrate 156 which increases the thickness of the metallic cutting blade 142 at the distal end thereof. The folded back portion 157 may comprise a sufficient length such that, when extended, the proximal edge 158 thereof is yet retained within the slot 107.

The facing edge bend 159 may comprise a plurality of apertures 160, thereby providing the substantially serrated edge especially suited for sideways cutting.

Figure 28:
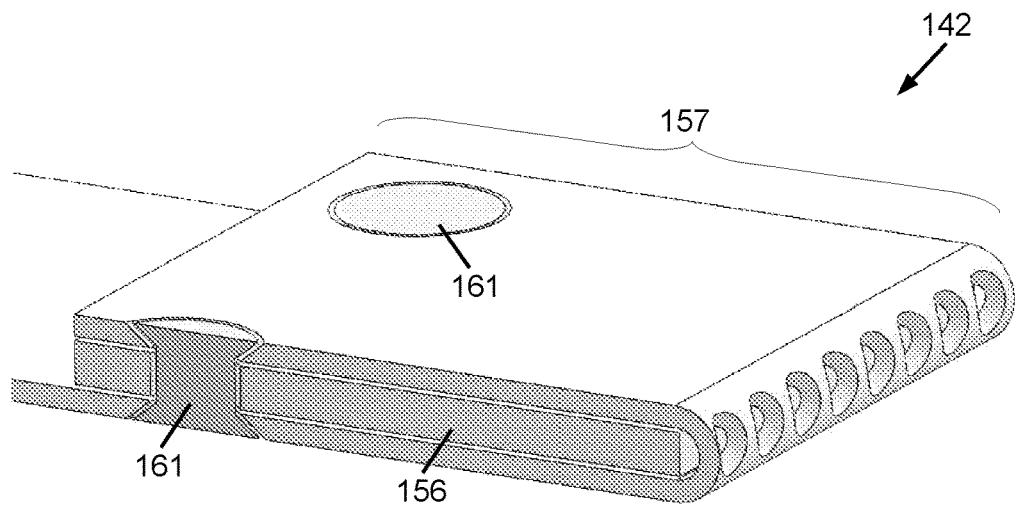
FIG. 28 shows a perspective view of the distal end of the cutting blade of the diathermy suction dissector apparatus.

FIG. 28 illustrates upper and lower portions of the metallic cutting blade 142 held in place with one or more ties 161 extending therethrough and through the substrate 156 also.

Figure 29:
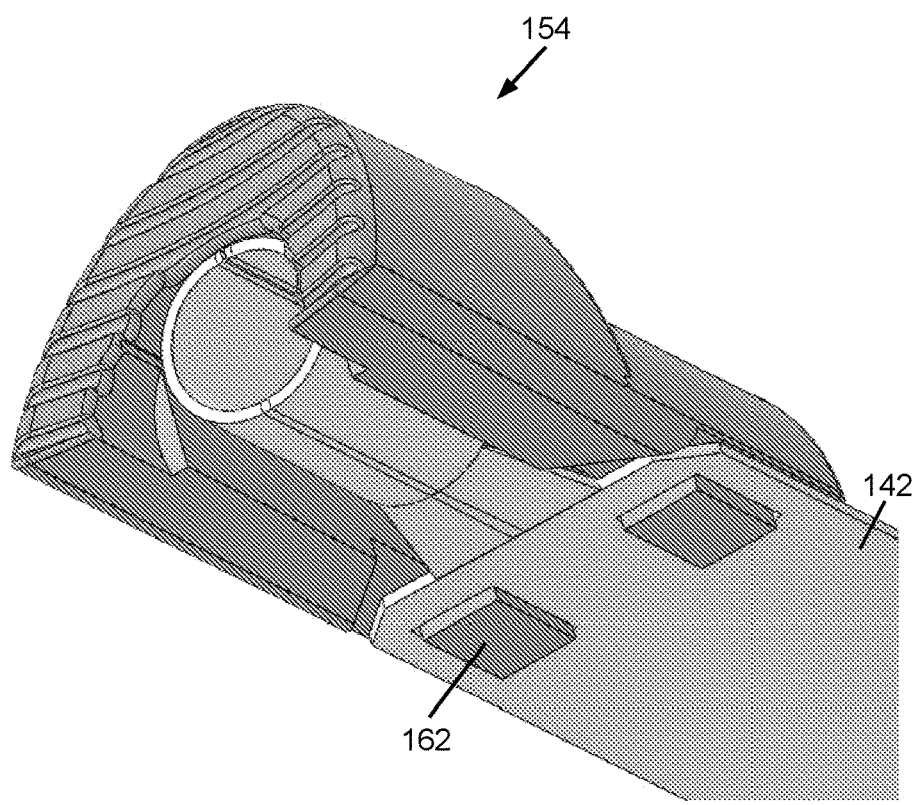
FIG. 29 illustrates an alternative embodiment of the plastic proximal button of the diathermy suction dissector apparatus in accordance with an embodiment.

FIG. 29 illustrates an alternative embodiment of the plastic proximal button 154 being of unitary construction (as opposed to the bifurcated construction as is illustrated in FIGS. 22 and 23). The plastic proximal button 154 may be retained by inferior square bosses 162 which extend through apertures of the metallic cutting blade 142.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. Diathermy tonsillectomy suction dissector apparatus comprising:
    a body having a proximal handle, the handle defining an elongate axis,
    a distal curved tip having a longitudinal axis extending from a proximal end to a distal end of the tip, a smooth, continuous curve in the distal curved tip being an inferiorly directed curve formed along the longitudinal axis, the inferiorly directed curve deviating the longitudinal axis of the distal curved tip from the elongate axis of the handle, and
    a diathermy cutting blade member slidably retained within the body to selectively extend from the tip, the blade extending flexibly along the inferiorly directed curve in the distal curved tip,
    wherein the diathermy cutting blade member comprises a flexible metallic blade comprising a proximal electrical connector female socket and a hand operable electrically insulative position locking mechanism attached to the blade, the locking mechanism hand operable via apertures and interlocking therewith to position the diathermy cutting blade member between retracted and extended positions and to lock the diathermy cutting blade member at the extended position,
    wherein, when in the extended position, the blade extends from the distal curved tip at an angle relative to the elongate axis of the handle,
    wherein the proximal electrical connector female socket is on a proximal end of the flexible metallic blade and wherein the proximal end of the flexible metallic blade extends from a rearward aperture of the handle,
    wherein an electrically insulative button conceals the electrical connector female socket therethrough and wherein the insulative button defines a rear face for pressing the cutting blade member towards the extended position,
    wherein the locking mechanism comprises a locking lever having a rearward knob and a catch,
    wherein the apertures comprise a proximal major aperture and a distal minor aperture,
    wherein, when the position locking mechanism is in the retracted position, the rearward knob and the catch locate in the proximal major aperture,
    wherein, when the position locking mechanism is in the extended position, the rearward knob locates in the proximal major aperture and the catch locates in the distal minor aperture,
    wherein the catch comprises an angled distal face, which slides under a distal edge of the major aperture when the cutting blade member moves towards the extended position;
    wherein the catch comprises a proximal edge which locks rearwardly against a proximal edge of the minor aperture when the position locking mechanism is in the extended position, wherein the lever is operable to be depressed to disengage the rearward knob from the proximal major aperture to remove the diathermy cutting blade member through the rearward aperture.

2. The apparatus as claimed in claim 1, wherein the blade is substantially planar and located within a rectangular cross-section slot.

3. The apparatus as claimed in claim 1, wherein the blade comprises aluminium.

4. The apparatus as claimed in claim 1, wherein sides of the blade form an encirclement forming the electrical connector female socket.

5. The apparatus as claimed in claim 4, further comprising an electrical connector comprising an electrode rod for insertion within the electrical connector female socket.

6. The apparatus as claimed in claim 5, wherein the electrical connector female socket has a diameter operable to receive the electrode rod therein and comprising an expansive longitudinal break.

7. The apparatus as claimed in claim 5, wherein the electrical connector comprises an angled boot which poises an electrical cable thereof at an angle from the electrode rod.

8. The apparatus as claimed in claim 1, further comprising a suction channel between at least one suction inlet port at the tip and a vacuum port at the handle.

9. The apparatus as claimed in claim 8, wherein the locking mechanism comprises bosses keying apertures of blade.

10. The apparatus as claimed in claim 8, wherein the locking mechanism engages a compression member to bias the locking mechanism proximally.

11. The apparatus as claimed in claim 1, further comprising a restraining wedge at a distal end of the blade.

12. The apparatus as claimed in claim 1, wherein the wedge is planar and is connected to the blade.

13. A diathermy tonsillectomy procedure using the apparatus as claimed in claim 1, the method comprising connecting an electrical supply lead to the electrical connector female socket of the blade and hand operation of the locking mechanism via the apertures to position the diathermy cutting blade member to an extended position such that blade extends from the tip.

14. A procedure as claimed in claim 13, wherein hand operation of the locking mechanism via the apertures to position the diathermy cutting blade member to the extended position comprises pressing a rearward insulative button of the diathermy cutting blade member.

15. A procedure as claimed in claim 14, further comprising hand operation of the locking mechanism via the apertures to position the diathermy cutting blade member to a retracted position comprising depressing a knob of a lever of the locking mechanism within a major aperture of the apertures such that a catch of the lever releases from a proximal edge of a minor aperture of the apertures.

* * * * *